United States Patent [19]
Willard et al.

[11] Patent Number: 5,536,242
[45] Date of Patent: Jul. 16, 1996

[54] INTRAVASCULAR DEVICE UTILIZING FLUID TO EXTRACT OCCLUSIVE MATERIAL

[75] Inventors: Kevin C. Willard, Osseo; Peter T. Keith, Fridley, both of Minn.

[73] Assignee: Scimed Life Systems, Inc., Maple Grove, Minn.

[21] Appl. No.: 547,964

[22] Filed: Oct. 25, 1995

Related U.S. Application Data

[63] Continuation of Ser. No. 269,715, Jul. 1, 1994, abandoned.

[51] Int. Cl.$^6$ .............................. A61M 1/00; A61M 3/00
[52] U.S. Cl. ............................. 604/30; 604/22; 604/35; 604/43; 604/40; 606/159; 606/170
[58] Field of Search ................................. 604/22, 27, 28, 604/30, 31, 33, 35, 40, 43; 606/159, 170

[56] References Cited

U.S. PATENT DOCUMENTS

| | | |
|---|---|---|
| 1,114,268 | 10/1914 | Kells . |
| 1,902,418 | 3/1933 | Pilgrim . |
| 3,526,219 | 9/1970 | Balamuth ................................. 604/22 |
| 3,805,787 | 4/1974 | Banko . |
| 4,024,866 | 5/1977 | Wallach . |
| 4,468,216 | 8/1984 | Muto . |
| 4,690,672 | 9/1987 | Veltrup . |
| 4,696,667 | 9/1987 | Masch ..................................... 604/22 |
| 4,913,698 | 4/1990 | Ito et al. . |
| 4,921,476 | 5/1990 | Wuchinich . |
| 4,935,006 | 6/1990 | Hasson . |
| 4,941,872 | 7/1990 | Felix et al. . |
| 4,950,238 | 8/1990 | Sullivan . |
| 5,037,431 | 8/1991 | Summers et al. . |
| 5,037,432 | 8/1991 | Molinari ................................ 604/35 |
| 5,100,425 | 3/1992 | Fischell et al. ........................ 604/22 |
| 5,135,482 | 8/1992 | Neracher . |
| 5,135,484 | 8/1992 | Wright . |
| 5,180,387 | 1/1993 | Ghajar et al. . |

(List continued on next page.)

FOREIGN PATENT DOCUMENTS

| | | |
|---|---|---|
| 0232678A2 | 8/1987 | European Pat. Off. . |
| 0470781A1 | 2/1992 | European Pat. Off. . |
| 0485133A1 | 5/1992 | European Pat. Off. . |
| 0489496A1 | 6/1992 | European Pat. Off. . |

OTHER PUBLICATIONS

"Rheolytic Catheter for Percutaneous Removal of Thrombus," Drasler et al., *Radiology*, 1992; 182: 1–5.
"The Clot Buster™," Amplatz Thrombectomy Device—3-page brochure.
"Human Percutaneous Thrombectomy Using the New Hydrolyser Catheter: Preliminary Results in Saphenous Vein Grafts," Coronary Surgery, pp. 378–383.
Product Brochure re. the AngioJet™ Rheolytic Thrombectomy System from Possis Medical Inc., 4 pages, 1993.
6–page brochure on the "Hydrolyser" by Cordis.
"What's new in interventional cardiology?" Clinica World Medical Device News, No. 570, pp. 18,19, Sep. 22, 1993.

*Primary Examiner*—John D. Yasko
*Assistant Examiner*—Laird J. Knights
*Attorney, Agent, or Firm*—Robert Atkinson

[57] ABSTRACT

An intravascular device and associated system which utilizes pressurized fluid to extract occlusive material. The device and system includes several unique features which provide desirable advantages over prior art devices. For example, the device is particularly suitable for removing occlusive material which is diffuse, friable, grumous-like, paste-like, granular, and/or chunky. The device includes independently movable fluid input and fluid output tubes and may be advanced over a guide wire. The fluid port holes are located immediately adjacent the distal end of the fluid output tube so as to engage the occlusive material without the need to first traverse the occlusive material with the device. The system utilizes a unique constant volume pump and associated pressure sensors to maintain balanced flow and immediately detect and correct conditions which may cause clinical complications.

39 Claims, 16 Drawing Sheets

U.S. PATENT DOCUMENTS

| | | |
|---|---|---|
| 5,195,955 | 3/1993 | Don Michael . |
| 5,201,723 | 4/1993 | Quinn . |
| 5,242,387 | 9/1993 | Loughlin .................................. 604/33 |
| 5,250,060 | 10/1993 | Carbo et al. . |
| 5,259,842 | 11/1993 | Plechinger et al. ........................ 604/43 |
| 5,318,518 | 6/1994 | Plechinger et al. ........................ 604/43 |
| 5,320,599 | 6/1994 | Griep et al. ................................ 604/43 |
| 5,370,609 | 12/1994 | Drasler et al. ............................. 604/43 |
| 5,391,145 | 2/1995 | Dorsey, III ................................ 604/33 |

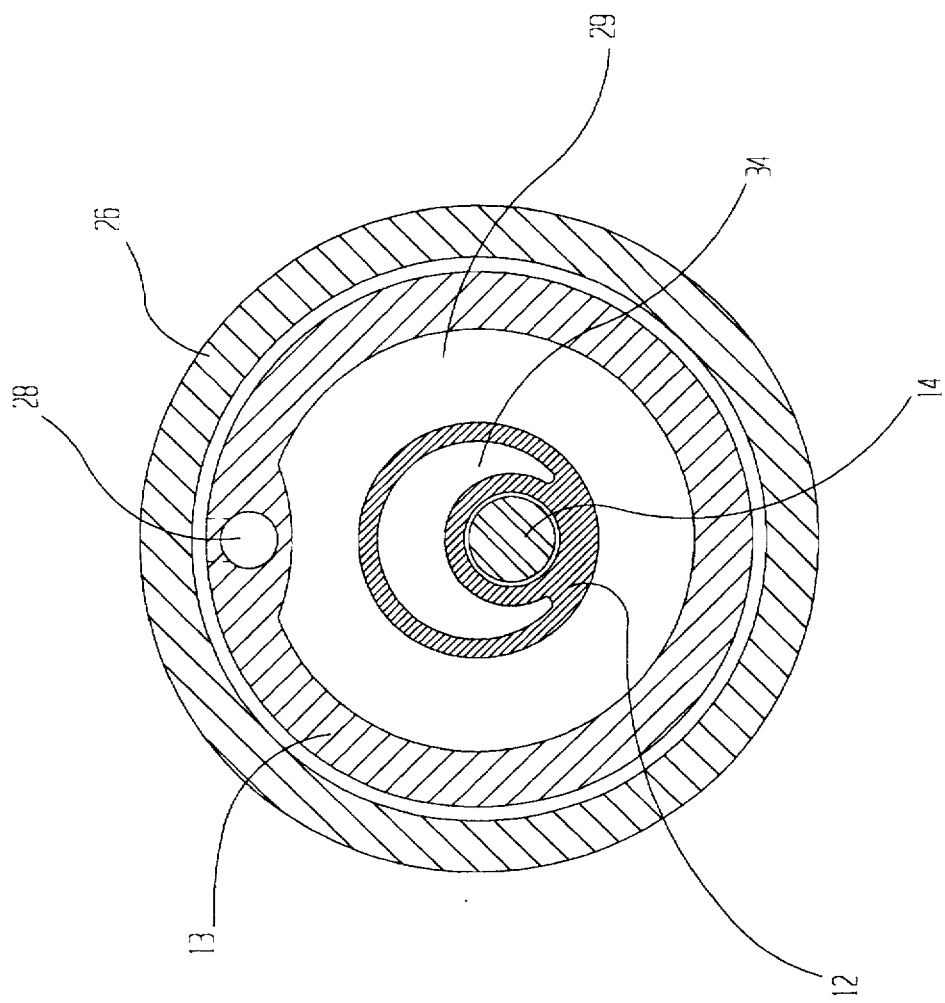

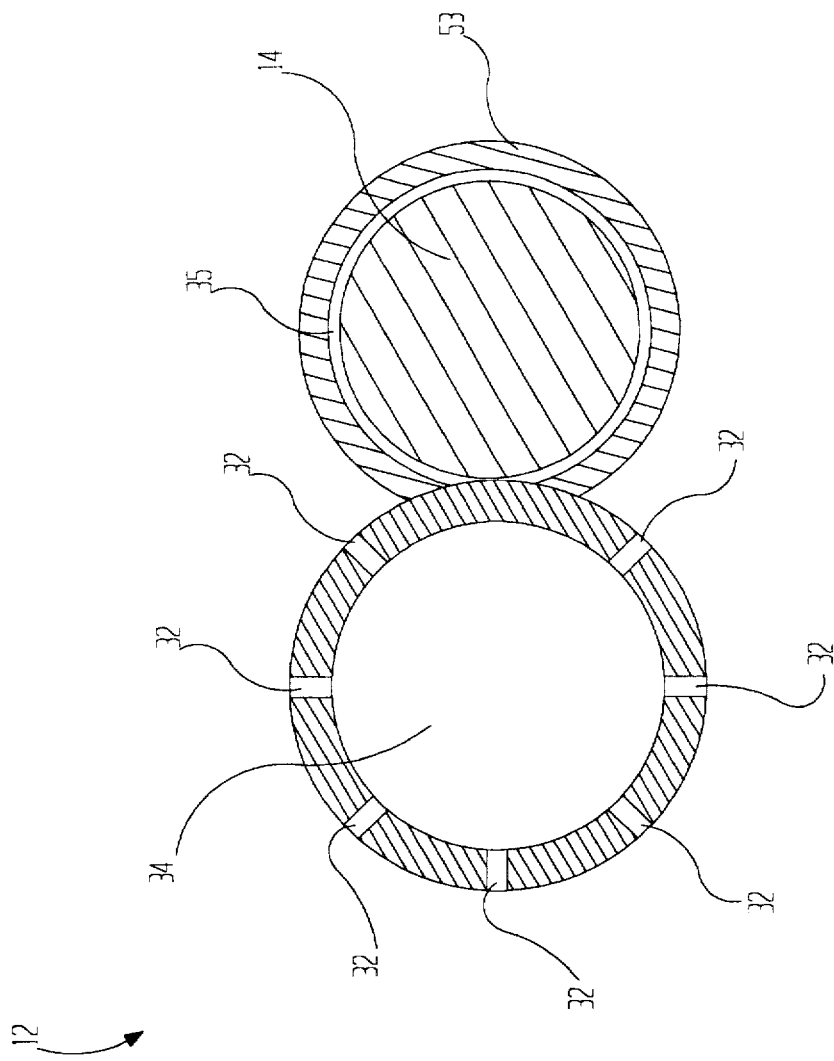

INTRAVASCULAR DEVICE UTILIZING FLUID TO EXTRACT OCCLUSIVE MATERIAL

This is a continuation of application Ser. No. 08/269,715, filed Jul. 1, 1994 now abandoned.

FIELD OF THE INVENTION

The present invention generally relates to intravascular devices for the removal of occlusive material. More specifically, the present invention relates to intravascular devices utilizing fluid to extract occlusive material and methods of use thereof. Those skilled in the art will recognize the benefits of applying the present invention to similar fields not discussed herein.

BACKGROUND OF THE INVENTION

A wide variety of therapeutic techniques have been developed to correct or inhibit vascular diseases. Coronary artery disease (CAD), for example, is an adverse condition of the heart in which the blood flow to the heart muscle is partially or totally restricted by occlusive material in the coronary arteries is which narrows the blood flow lumen. The occlusive materials deprive portions of the heart muscle of essential oxygenated blood.

CAD may be treated by a surgical technique referred to as coronary artery bypass graft (CABG) surgery. This surgical procedure involves supplementing blood flow to the heart muscle by grafting non-native conduit such as a saphenous vein graff (SVG) to the heart. A first end of the SVG is connected to the ascending aorta (proximal to the occlusive material) and the other end is connected to the artery distal of the occlusive material. Although this technique has been useful for treating CAD in native coronary arteries, it is not uncommon for occlusive material to form over time in the SVG thereby necessitating additional therapy. Typically, the nature of the occlusive material in the new SVG may be diffuse, friable, grumous-like, paste-like, granular, and/or chunky.

Percutaneous translumenal coronary angioplasty (PTCA) has gained wide acceptance as an effective and less invasive alternative to CABG surgery in certain patient groups. The PTCA procedure involves the use of an angioplasty balloon catheter, several types of which are well known in the art. The balloon catheter is inserted into the body via the femoral artery and navigated to the coronary arteries assisted by a guide catheter and (usually) a guide wire. The balloon is positioned across the restriction in the artery and subsequently inflated. The inflated balloon widens the restriction and restores blood flow to portions of the heart muscle previously deprived of oxygenated blood.

Although balloon PTCA has been demonstrated to be clinically effective in treating a wide variety of vascular restrictions, there are alternative devices and techniques which are specially adapted to treat lesions with complex morphology and/or unique pathology. For example, SVGs commonly contain abnormal deposits which are diffuse, degenerated, and thrombus-containing. Because treating an SVG lesions with balloon PTCA has an unfavorably high incidence of distal embolization, alternative therapies such as atherectomy have been favored.

Atherectomy (or thrombectomy) is an alternative to balloon PTCA and targets specific types of lesion morphology and pathology. Atherectomy, as distinguished from balloon PTCA, removes the occlusive material from the local vasculature rather than molding or reshaping the restriction by compression. While some prior art atherectomy devices have been specifically indicated to be effective for treating certain types of diseased SVGs, the incidence of complications (e.g. distal coronary artery embolization, cerebral embolization via the aorta) has been reported to be suboptimally high. Thus, there is a need for an improved atherectomy or thrombectomy device for the removal occlusive material, particularly in friable, diffusely diseased SVGs.

Several prior art atherectomy or thrombectomy devices utilize concepts of fluid jets to remove occlusive material. For example, EPO Application 470,781 A1 to Drasler discloses a device which uses high pressure water jets to remove occlusive material. The high pressure water jet is directed proximally to dislodge and emulsify thrombus. However, because of the high pressures associated with this device and the corresponding risk of damage to the vessel wall if exposed to the high pressure jet, the water jet is only exposed through a laterally facing window in a protective housing. Since the effective cutting area is limited to the size of the window, multiple passes are required to remove occlusive material deposited around the inner circumference of the vessel. Furthermore, because the device utilizes a prospective housing, a portion of the device must first traverse the occlusion before the water jet is able to dislodge and emulsify the occlusive material. This unnecessarily increases the risk of distal embolization and increases the difficulty in crossing a tight occlusion.

A similar high pressure water jet atherectomy device is disclosed in EPO Application 485,133 A1 to Drasler. This water jet atherectomy device also utilizes a very high pressure (more than 3,500 psi) water jet which is directed distally or proximally within a protective housing. This device further includes a biasing balloon which permits asymmetric or directional atherectomy. Once again, because of the high pressures associated with this device and the corresponding risk of damage to the vessel wall if exposed to the high pressure, the cutting area is essentially limited to the open window in the protective housing. Since the effective cutting area is limited to the size of the window, multiple passes are required to remove occlusive material deposited around the inner circumference of the vessel. Furthermore, because the device utilizes a protective housing, a portion of the device must first traverse the occlusion before the water jet is able to dislodge and emulsify the occlusive material. As stated earlier, this unnecessarily increases the risk of distal embolization and increases the difficulty in crossing a tight occlusion.

A further example of a high pressure water jet atherectomy device is disclosed in EPO Application 489,496 A1 to Drasler. This water jet atherectomy device also utilizes a very high pressure (more than 3,500 psi) water jet directed distally to dislodge and emulsify thrombus. The jet stream is directed distally to permit the ablation of a total occlusion without requiring the distal end of the device to first cross the occlusion. However, because of the distally directed high pressure water jet used in this device, damage to the vessel wall is risked for lack of a protective shield. Furthermore, the distally directed water jet tends to flush the dislodged material in a distal direction which may result in undesirable embolization.

Another pressurized (440 psi minimum pressure source) fluid device is disclosed in U.S. Pat. No. 4,690,672 to Veltrup. This device directs a fluid stream proximally into a mouth of a suction tube and removes unwanted material when the material is in juxtaposition with the mouth of the suction tube. Similar disadvantages are associated with this device. For example, the cutting diameter is essentially limited to the size of the opening, which is less than the diameter of the catheter shaft. Additionally, no occluding balloon is provided which increases the risk of simply draining blood from the occluded vessel. Also, no guide wire is provided to guide the catheter within the vasculature, thus intravascular navigation would be significantly limited.

A further limitation common to several of the above-cited fluid jet atherectomy devices is that the fluid input lumen and the effluent lumen are longitudinally fixed relative to each other. More specifically, the fluid input lumen and the effluent lumen can not be longitudinally moved independently. This requires the relatively large effluent lumen to be advanced along with the fluid input lumen. Since the effluent lumen is relatively large and stiff, the distance the device can be advanced into tortuous and/or small diameter vessels is limited. Additionally, the fluid input lumen can not be retracted into the extraction lumen to clean up clogging debris.

In view of the unresolved disadvantages of each of these devices, it is desirable to have a device which utilizes a relatively low fluid pressure to minimize the risk of causing damage to the vessel wall. It is also desirable to have a device which directs fluid laterally rather than proximally or distally. Laterally directed fluid allows the device to dislodge material immediately adjacent the distal end of the device without first traversing the occlusion and also reduces the risk of distal embolization. It is further desirable to have a device which utilizes independently movable fluid input and fluid extraction lumens to maximize vascular accessibility and remove clogs that form in the extraction lumen.

SUMMARY OF THE INVENTION

The present invention overcomes the competing disadvantages of the prior art in a novel and non-obvious manner. One embodiment of the present invention is a fluid system used to extract vascular occlusion material, and includes a long catheter shaft having a fluid input lumen and an extraction lumen extending therethrough. A pressurized fluid source is connected to the proximal end of the shaft and is in fluid communication with the fluid input lumen. A pressurized fluid collector is connected to the proximal end of the shaft and is in fluid communication with the extraction lumen. A nozzle is attached to the distal end of the shaft and is in fluid communication with the fluid input lumen. A control system is operatively connected to and controls the pressurized fluid source and the pressurized fluid collector as a function of fluid dynamic parameters in the fluid input lumen and the extraction lumen.

Another embodiment of the present invention is a fluid system which includes an elongate extraction tube having an extraction lumen extending therethrough and a fluid input tube coextending with the extraction tube and longitudinally movable relative thereto. The fluid input tube has a fluid input lumen extending therethrough. A pressurized fluid source is connected to the proximal end of the fluid input tube and is in fluid communication with the fluid input lumen. A pressurized fluid collector is connected to the proximal end of the extraction tube and is in fluid communication with the extraction lumen. A guide wire is positioned so as to coextend with the fluid input tube and is also longitudinally movable relative thereto. A nozzle is connected to the distal end of the fluid input tube and is in fluid communication with the fluid input lumen.

Yet another embodiment of the present invention is a fluid system including an elongate catheter shaft having a fluid input lumen and an extraction lumen extending therethrough. A pressurized fluid source is connected to the proximal end of the shaft and is in fluid communication with the fluid input lumen. A pressurized fluid collector is connected to the proximal end of the shaft and is in fluid communication with the extraction lumen. A nozzle is attached to the distal end of the shaft and is in fluid communication with the fluid input lumen. At least one port hole is located about the circumference of the nozzle and is directed laterally such that the axis of the hole is at an angle of about 90 degrees with the longitudinal axis of the shaft. The fluid exiting the port hole defines a cutting diameter which is greater than the outside diameter of the catheter shaft adjacent to the nozzle.

A further embodiment of the present invention is a fluid system for the extraction of vascular occluding material wherein the vasculature has a first pressure zone with a first pressure (P1) proximal to the occluding material, and a second pressure zone with a second pressure (P2) adjacent the occluding material. The fluid system includes a catheter shaft having a fluid input lumen and an extraction lumen extending therethrough. A pressurized fluid source is connected to the proximal end of the shaft and is in fluid communication with the fluid input lumen. A pressurized fluid collector is connected to the proximal end of the shaft and is in fluid communication with the extraction lumen. A nozzle is attached to the distal end of the shaft and is in fluid communication with the fluid input lumen. A control system controls the pressurized fluid source and the pressurized fluid collector as a function of at least one of the pressures (P1 or P2).

In practice, a method of using a fluid system for the extraction of vascular occluding material wherein the device includes an extraction tube having an extraction lumen extending therethrough, a fluid input tube having a fluid input lumen extending therethrough and being longitudinally movable relative to the extraction tube, a pressurized fluid source connected to the proximal end of the fluid input tube and in fluid communication with the fluid input lumen, a pressurized fluid collector connected to the proximal end of the extraction tube and in fluid communication with the extraction lumen, a guide wire coextending with the fluid input tube and longitudinally movable relative thereto, and a nozzle connected to the distal end of the fluid input tube and in fluid communication with the fluid input lumen, the method of use includes the steps of: (1) Inserting the guide wire into the fluid input tube, (2) advancing the guide wire, the fluid input tube and the extraction tube into a vascular lumen, (3) positioning the distal end of the extraction tube proximal to an occlusion to be removed, (4) positioning the distal end of the fluid input tube adjacent the occlusion to be removed, and (5) activating the pressurized fluid source and the pressurized fluid collector.

While the disclosure focuses on intravascular fluid devices, one skilled in the art will recognize that the invention may be incorporated into other apparatus and methods of use not discussed herein. Furthermore, in addition to the advantages described, other advantages of the present invention may be appreciated without departing from the spirit of the invention.

BRIEF DESCRIPTION OF THE DRAWINGS

FIG. 3 is a cross sectional view taken at 3—3 in FIG. 2a and at 3—3 in FIG. 2b.

DETAILED DESCRIPTION OF THE INVENTION

The following detailed description should be read with reference to the drawings in which like elements in different figures are numbered identically.

Specific materials, dimensions and manufacturing processes are provided for selected design elements. Those design elements which do not have specific materials, dimensions or manufacturing process identified, employ that which is well known to those skilled in the field of the invention. In addition, those skilled in the art will recognize many of the materials, dimensions and manufacturing processes identified are exemplary, for which suitable alternatives may be utilized.

Figure 1A:
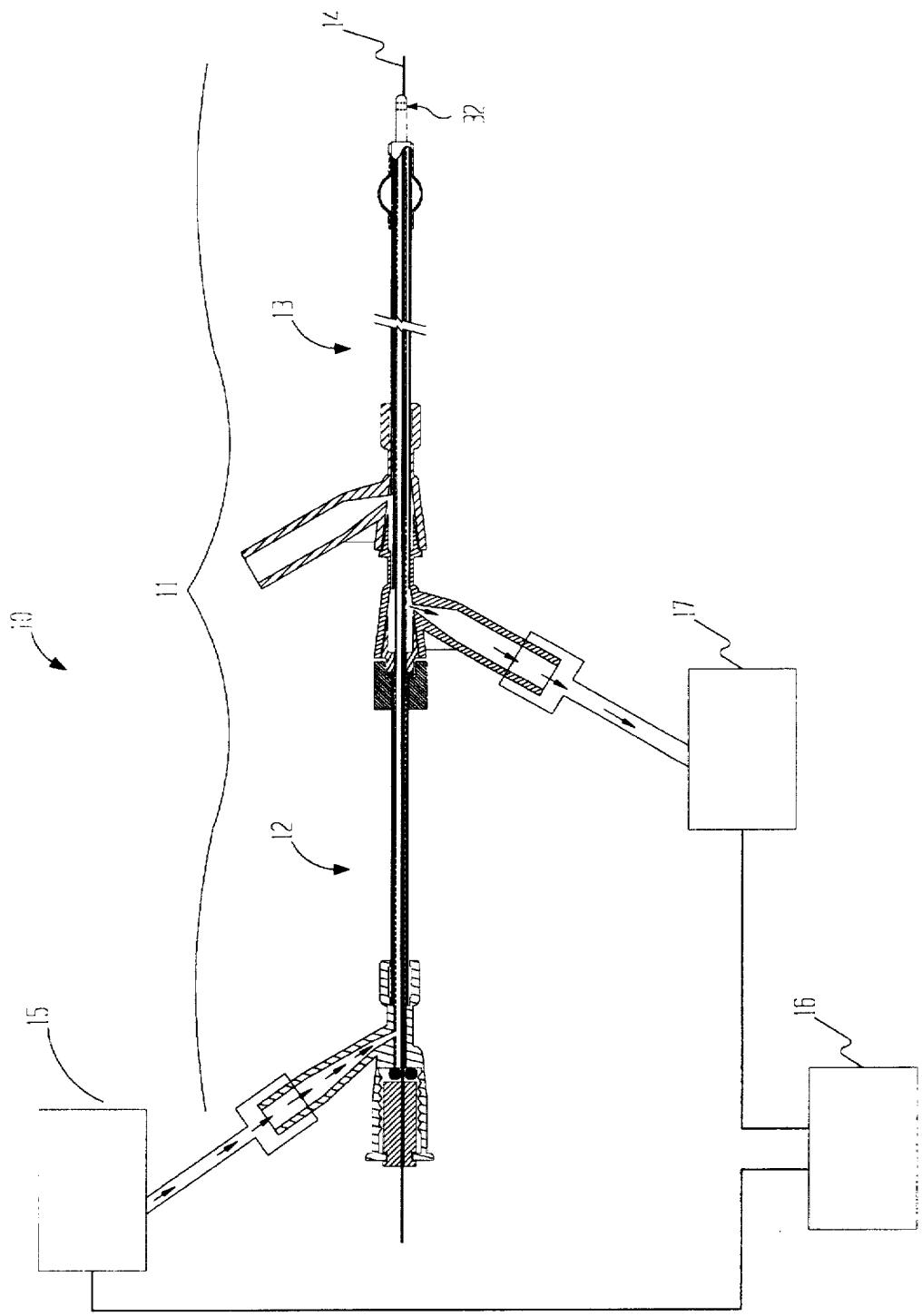
FIG. 1a is a plan view of a first embodiment of the present invention.
Figure 1B:
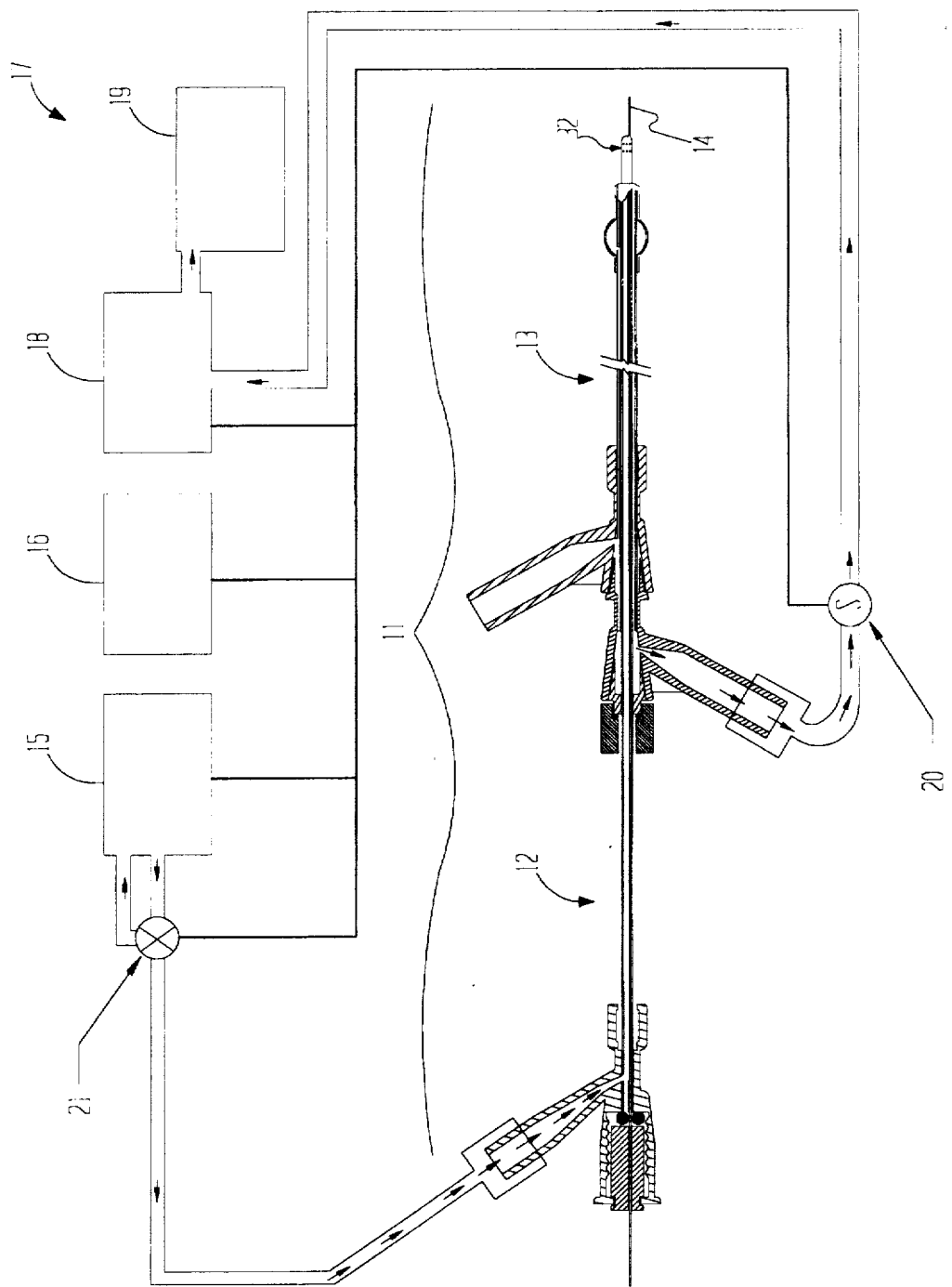
FIG. 1b is a plan view of a second embodiment of the present invention.
Figure 1C:
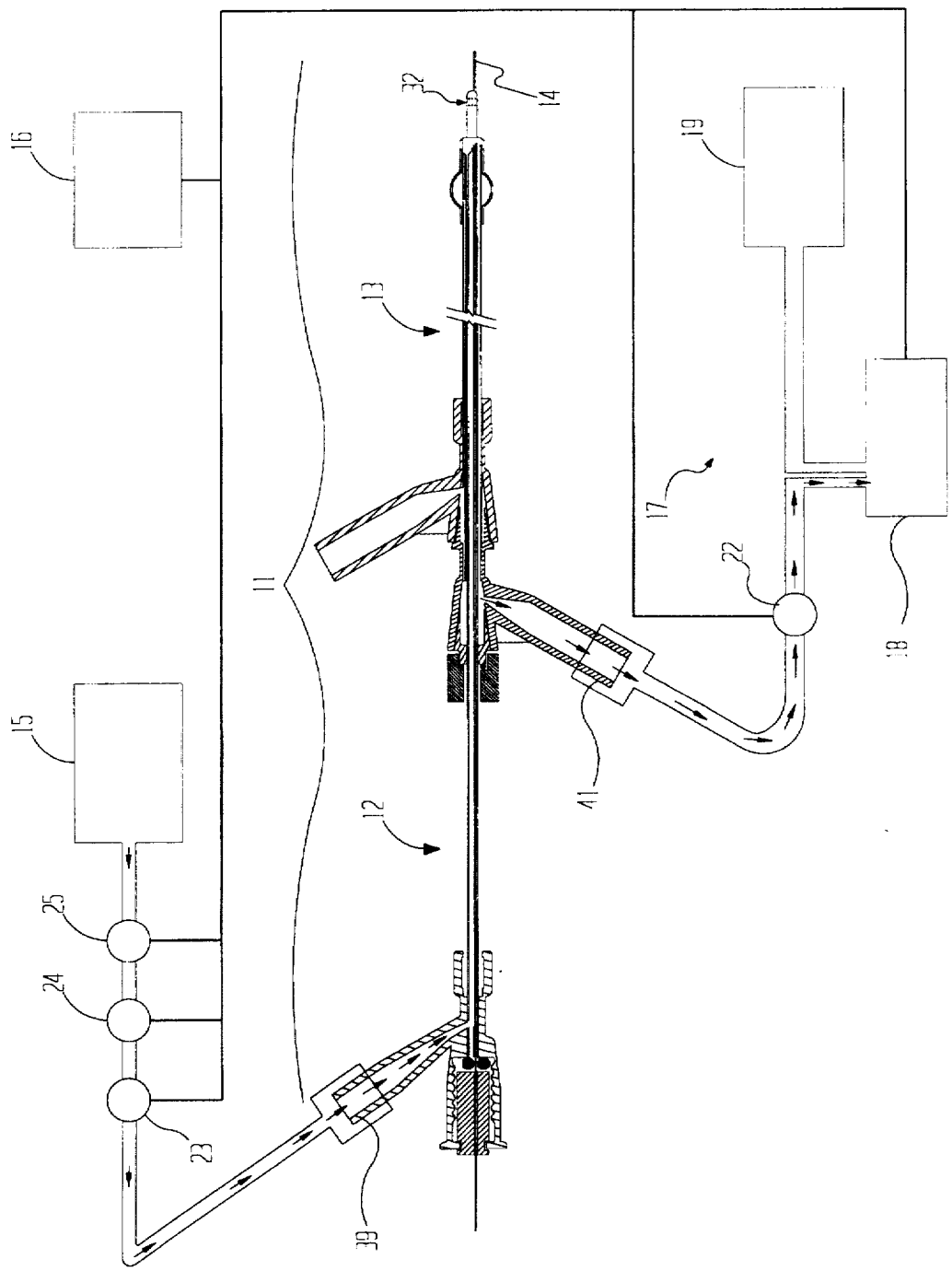
FIG. 1c is a plan view of a third embodiment of the present invention.
Figure 2A:
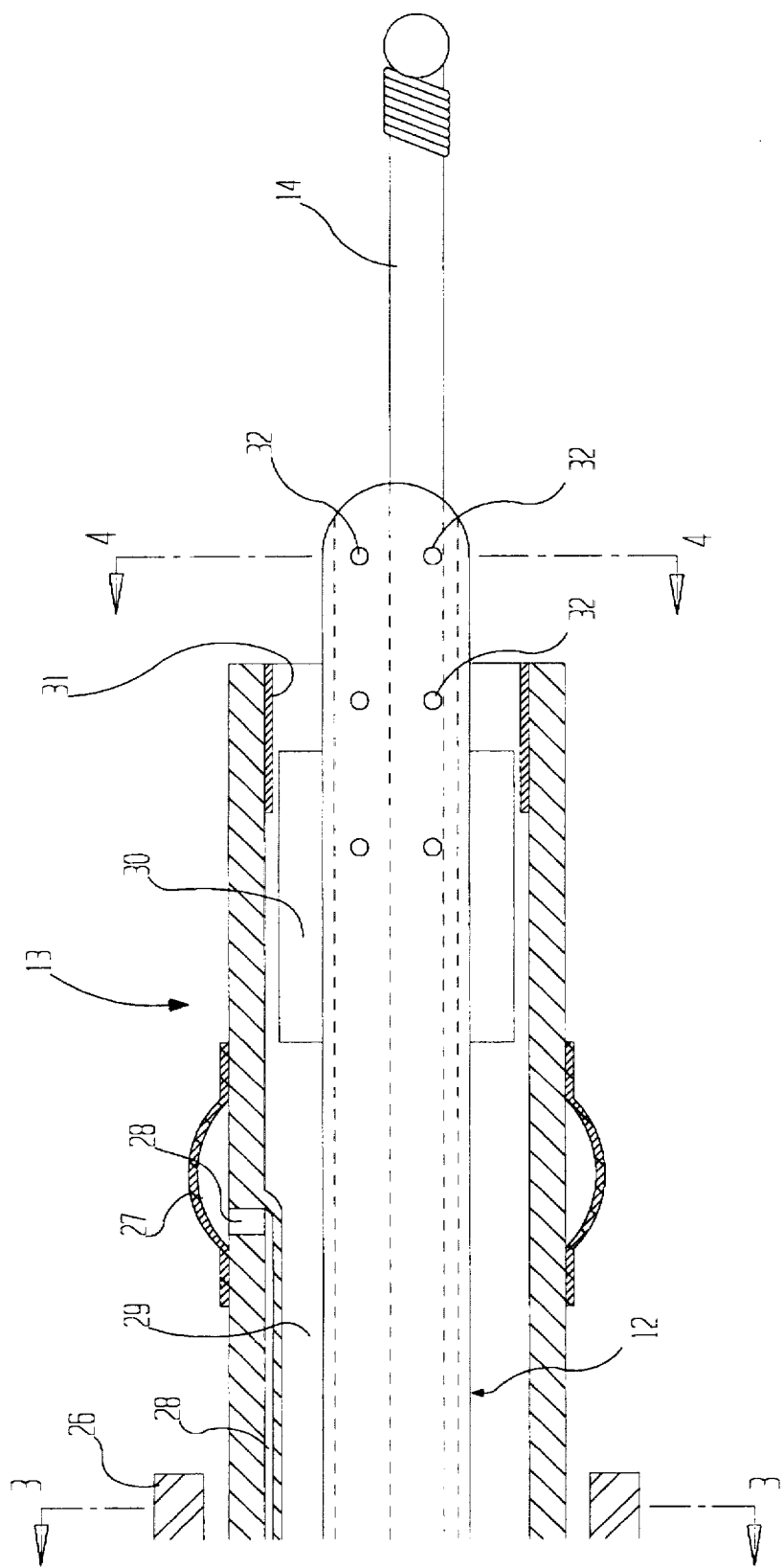
FIG. 2a is a longitudinally partially sectioned view of a first embodiment of a catheter of the present invention.
Figure 2B:
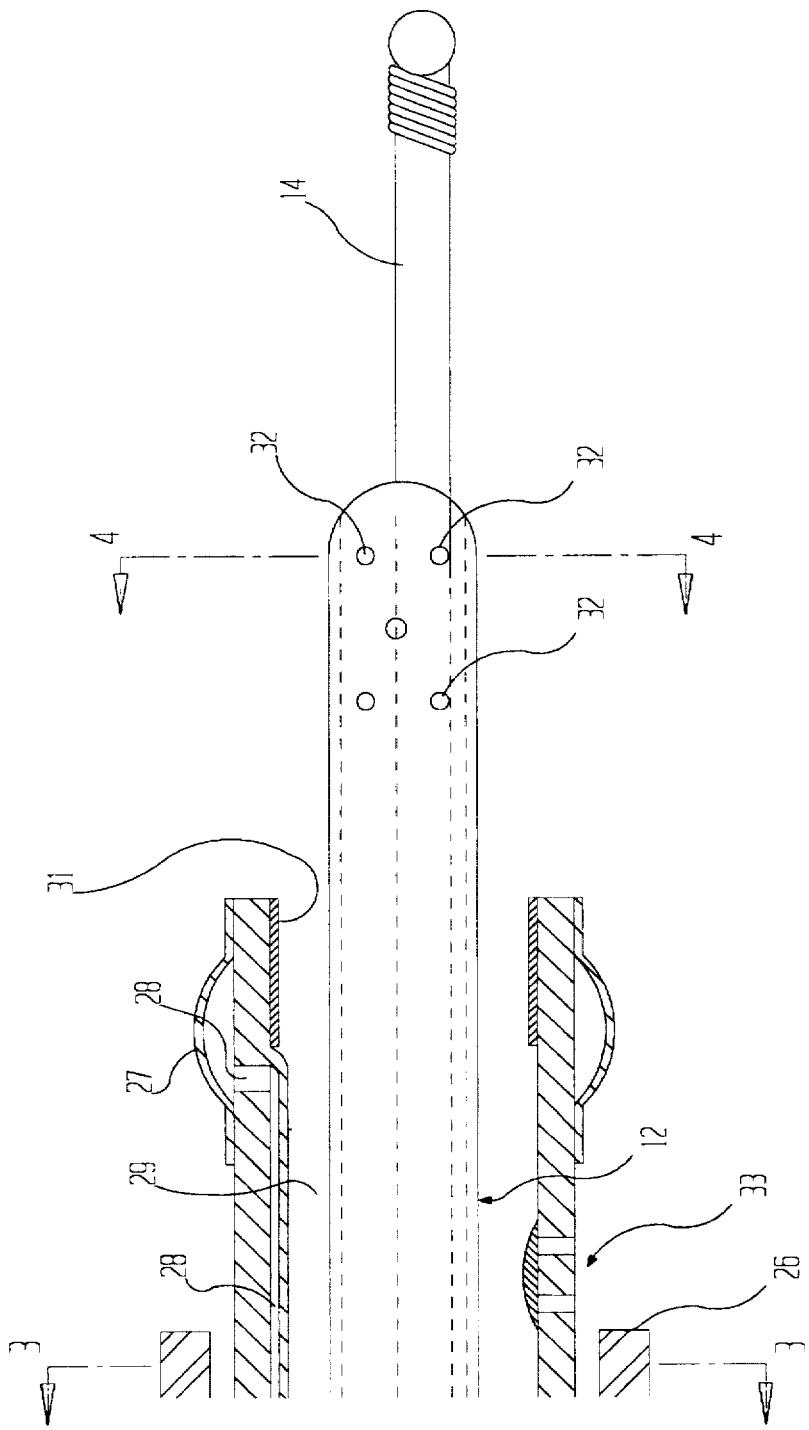
FIG. 2b is a longitudinally partially sectioned view of a second embodiment of a catheter of the present invention.

Referring to FIG. 1a, a plan view of a first embodiment of the fluid system 10 is shown. The basic fluid system 10 includes a catheter system 11, a pressurized fluid source 15, a pressurized fluid collector 17, and a control system 16. The catheter system 11 includes a port tube 12 (also referred to as fluid input tube), an aspiration tube 13 (also referred to as extraction tube), and a guide wire 14. Catheter system 11 may be used in combination with a guide catheter 26 (as shown in FIGS. 2a and 2b) to facilitate navigation in the coronary artery system. The pressurized fluid source 15 operates between about 1 and 2500 psi, preferably 500 and 1500 psi, and causes pressurized fluid to be supplied into the port tube 12 and exit its distal end through port holes 32. The pressurized fluid is preferably a saline solution but may also include therapeutic agents, heparin, and/or an abrasive suspension. The pressurized fluid collector 17, by way of extraction tube 13, removes the fluid exiting port holes 32 as well as any dislodged occlusive material. The pressurized fluid collector 17 may operate at pressures less than atmospheric pressure (i.e. a vacuum) or at pressures near atmospheric pressure. The control system 16 maintains volumetric flow equilibrium between the pressurized fluid source 15 and the pressurized fluid collector 17 so as to prevent distal embolization, vessel rupture and vessel collapse. A detailed description of the control system 16 and the alternate fluid systems 10 shown in FIGS. 1b and 1c is discussed after the following detailed description of catheter system 11.

The catheter system includes extraction tube 13, as best shown in FIG. 2a, which in turn includes an occluding balloon 27 mounted on its distal end and in fluid communication with the balloon inflation lumen 28. The occluding balloon 27 serves to isolate the vascular site and prevent blood from flowing distally thereof and also prevents retrograde flow of dislodged debris. An occluding balloon (not shown) may also be included on the port tube 12 to further isolate the treatment site. Extraction tube 13 further includes an extraction lumen 29 extending along its entire length. An aspiration window 30 is positioned immediately proximal of the distal annular opening defined between the port tube 12 and the extraction tube 13. Preferably two aspiration windows 30 are utilized and placed on opposite sides of the extraction tube 13. Aspiration window 30 provides additional surface area so as to accommodate dislodged occlusive material of a size which may be larger than the annular opening between the port tube 12 and distal end of the aspiration tube 13. Additionally, aspiration window 30 provides a safety mechanism whereby if the annular opening at the distal end of the extraction tube 13 becomes clogged, fluid may still be removed through the aspiration window 30 and into the extraction lumen 29. This reduces the risk of causing distal embolization and vascular rupture. Extraction tube 13 also includes a radiopaque marker band 31 secured to its distal end. The radiopaque marker band 31 allows the physician to radiographically determine the position of the catheter system 11 and in particular, the vascular extraction tube 13. In addition, a radiopaque marker band (not shown) may be located on the distal end of the port tube 12, substantially as described above.

Extraction tube 13 is preferably made of a dual-lumen extruded polymer with an outer diameter of about 2.34 mm, a balloon inflation lumen 28 diameter of about 2.46 mm, and an extraction lumen 29 cross-sectional area of about 3.0 mm$^2$. The extraction tube 13 is preferably made of a polymer such as high density polyethylene, a blend of low density and high density polyethylene, or a blend of a polyetheter/polyamide polyester and high density polyethylene, and may include tapers along its length of preferably 133 cm. Occluding balloon 27 is preferably made of a thin-walled polymer such as an ionomer and has a deflated and wrapped outer diameter of 0.097 inches and a maximum expanded diameter of 6 mm at preferably 28 psi. The guide catheter 26 inside diameter must be sized to provide sufficient clearance around the deflated occluding balloon 27 to allow for the injection of contrast fluid. Occluding balloon 27 is preferably secured to the extraction tube 13 by means of a suitable adhesive such as a two-part urethane or by means of a thermal bonding process. Aspiration window 30 preferably includes two oppositely-facing windows with a length of 2.5 mm and a height of 2 mm. The aspiration window 30 is preferably formed in the extraction tube 13 by means of a punching process. Marker band 31 is preferably made of a radiopaque alloy such as 90% platinum+10% iridium, but other suitable dense metals such as gold, or platinum may be employed. Radiopaque marker band 31 preferably has a length of 1.3 mm, an outer diameter of 2.1 mm, and an inner diameter of 2.0 mm. The radiopaque marker band 31 is secured to the inner surface of the extraction tube 13 by a suitable adhesive such as a two-part epoxy.

Referring to FIG. 2b, an alternate embodiment of the extraction tube 13 is shown. All aspects of the aspiration tube 13 are identical to those described with reference to FIG. 2a, with the exception of bypass valve 33 which is used either in place of or in addition to aspiration window 30. The bypass valve 33 incorporates a hinged flap which allows fluid to pass in one direction. The bypass valve may be located on either side (interior/exterior) of the extraction tube 13 or on both sides. In the event that excess fluid is being extracted, bypass valve 33 allows fluid (probably blood) to enter the extraction lumen 29 in order to avoid vessel collapse. Alternatively, in the event that excess fluid is being delivered or the extraction lumen 29 becomes clogged, the bypass valve 33 allows fluid to escape the extraction lumen 29 in order to avoid vessel rupture and/or distal embolization. Thus, bypass valve 33 reduces the potential for distal embolization, vascular collapse and vascular rupture.

Figure 4A:
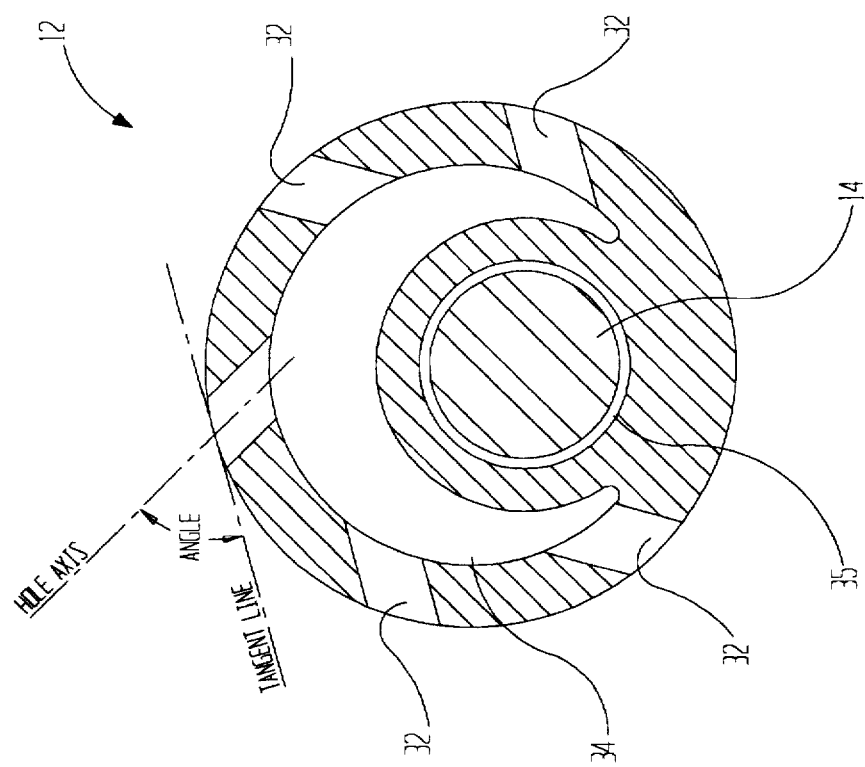
FIG. 4a is a cross sectional view of a first embodiment of a port tube of the present invention taken at 4—4 in FIG. 2a and 4—4 in FIG. 2b.

Referring to FIGS. 2a, 2b and 4a, a port tube 12 is shown which is slidably disposed in extraction tube 13. A guide wire is also slidably disposed in extraction tube 13 either adjacent to or within port tube 12. The port tube 12 may be made of a dual lumen extrusion and includes a fluid input lumen 34 and a guide wire lumen 35 as best shown in FIG. 4a. The port tube 12 is preferably made of extruded high density polyethylene wrapped with stainless steel wire coated with polyurethane and has an outer diameter of 1.3 mm, a guide wire lumen 35 diameter of 0.5 mm, and a fluid input lumen 34 cross-sectional area of 0.4 mm². Port tube 12 includes a plurality of port holes 32 (collectively referred to as a nozzle) which are formed in the distal end of the port tube 12 by a punching process or a drilling process. The distal end of fluid input lumen 34 is plugged with a suitable adhesive such as two-part urethane to force pressurized fluid through port holes 32. The nozzle may be made integral with the port tube 12 as discussed or may be made a separate element attached to the distal end of port tube 12. Port holes 32 are preferably spaced in three circumferential rows with preferably four to eight holes per row. The number of rows and number of holes per row can be adjusted to affect the size and geometry of the spray field. Port holes 32 preferably have an inner diameter of 0.6 mm and are laterally directed at a 90-degree angle relative to the longitudinal axis of the port tube 12 and directed at a 60-degree angle relative to a tangent line on the outer surface of the port tube 12. The laterally-directed ports 32 allow the pressurized fluid exiting through the port holes 32 to engage the occlusive material without the need to substantially traverse the occlusion with the distal end of port tube 12. In addition, since the port holes 32 are not directed distally, the momentum of the pressurized fluid does not force the dislodged occlusive material distally. Furthermore, because port holes 32 are directed at an angle to a tangent line on the outer surface of port tube 12, the impact of pressurized fluid against the vessel wall is diverted and thus the potential for trauma to the vessel wall is minimized. This angular orientation of port holes 32 also creates a spiral flow pattern which adds to the effect of the pressurized fluid.

Figure 4B:
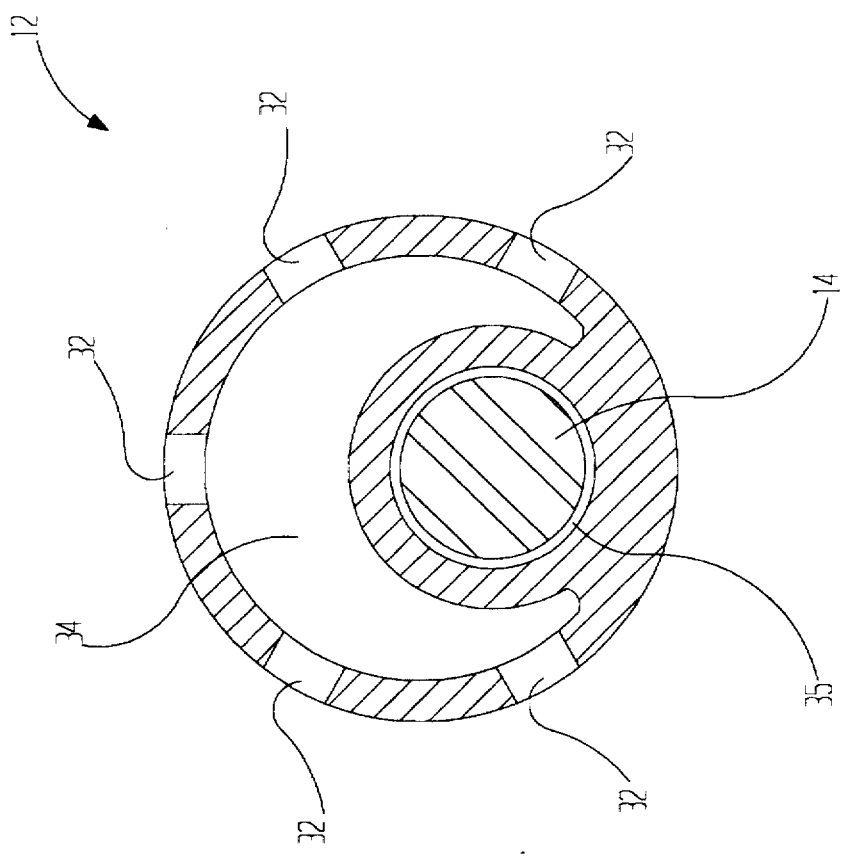
FIG. 4b is cross sectional view of a second embodiment of a port tube of the present invention taken at 4—4 in FIG. 2a and at 4—4 in FIG. 2b.

With reference now to FIG. 4b, a second embodiment of the port tube 12 is shown with port holes 32 directed proximally at an acute angle relative to the longitudinal axis of the port tube 12 and orthogonally relative to a tangent line on the outer surface of port tube 12. This orientation of port holes 32 causes the pressurized fluid to force dislodged occlusive material proximally toward the extraction tube 13. In addition, since port holes 32 are directed at an acute angle relative to the longitudinal axis of the port tube 12, the impact of pressurized fluid against the vessel wall is diverted and thus the potential for trauma to the vessel wall is minimized.

Figure 4C:
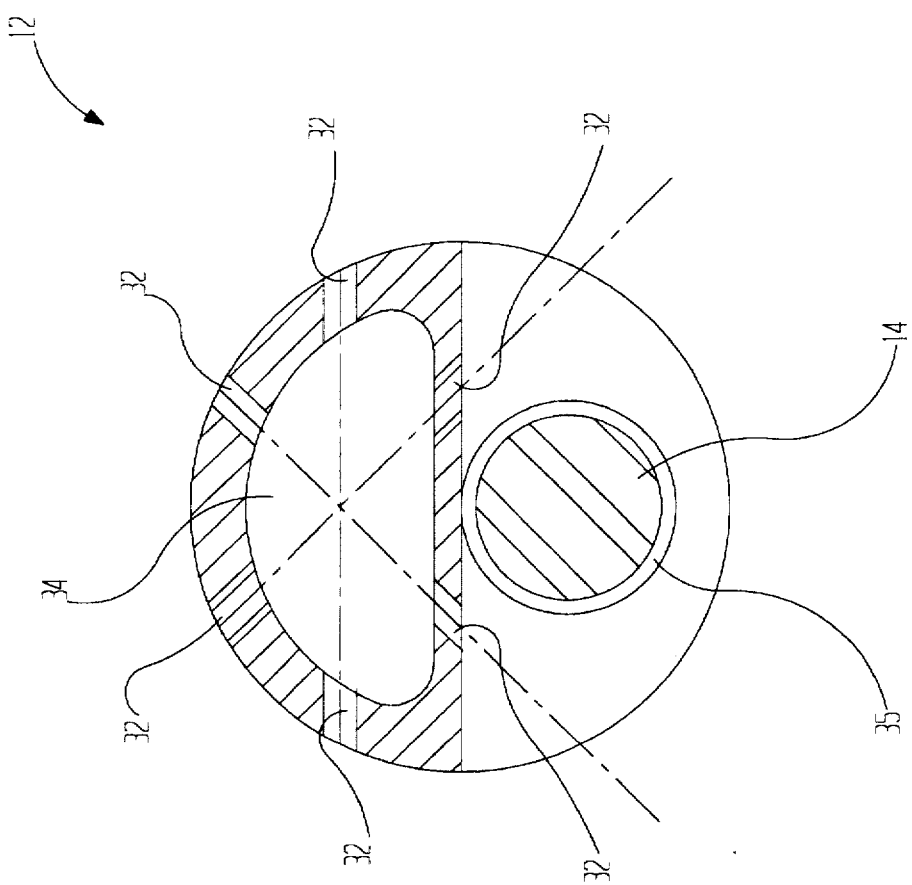
FIG. 4c is a cross sectional view of a third embodiment of a port tube of the present invention taken at 4—4 in FIG. 2a and at 4—4 in FIG. 2b.

FIG. 4c shows a third embodiment of the port tube 12. In this embodiment, port holes 32 are arranged to provide a circumferentially-even distribution of pressurized fluid. As compared to the embodiments shown in FIGS. 4a and 4b, the embodiment as shown in FIG. 4c eliminates the "blind spot" created by the presence of guide wire lumen 35 and guide wire 14. Preferably six port holes 32 are arranged in each circumferential row.

Figure 4D:
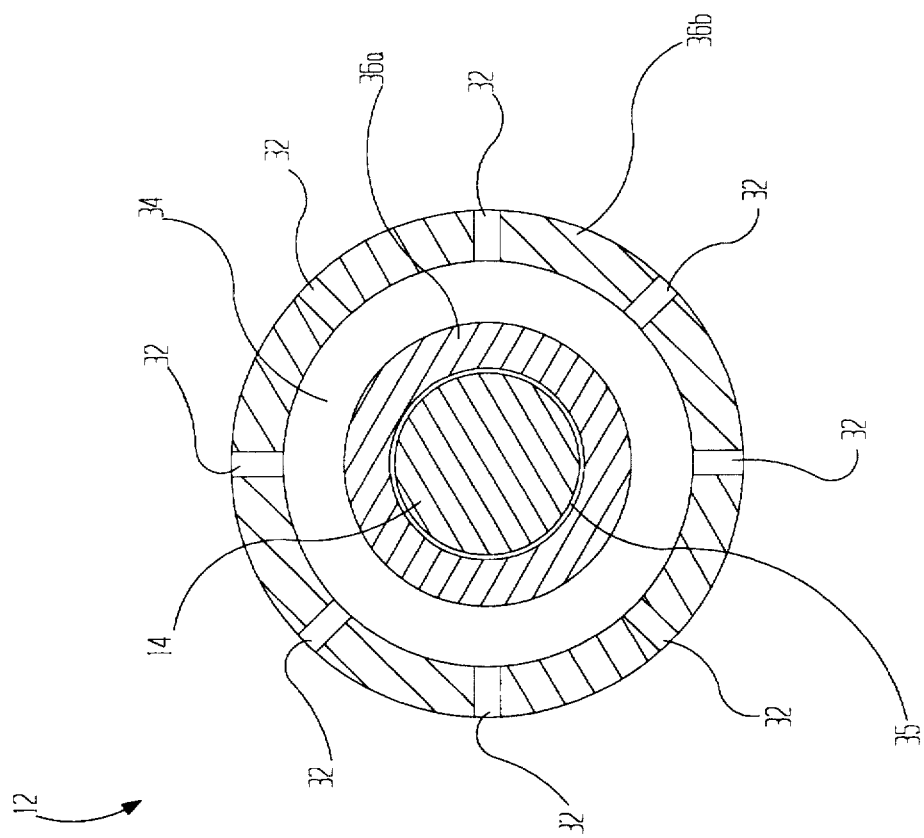
FIG. 4d is a cross sectional view of a fourth embodiment of a port tube of the present invention taken at 4—4 in FIG. 2a and at 4—4 in FIG. 2b.

FIG. 4d shows a fourth embodiment of the port tube 12 which includes an inner tube 36a and an outer tube 36b. The inner tube 36a is dimensioned to accommodate a guide wire 14 and is coaxially disposed within outer tube 36b. The outer tube 36b includes a plurality of port holes 32 equally spaced in preferably three rows of eight holes per row. Both inner tube 36a and outer tube 36b are made from an extruded polymer such as high density polyethylene. The inner diameter of inner tube 36a is the same as the diameter of guide wire lumen 35 as discussed above. The cross-sectional area of fluid input lumen 34 is substantially the same as described above with reference to FIG. 4a. The coaxial arrangement of inner tube 36a and outer tube 36b provides uniform lateral flexibility.

Figure 4E:
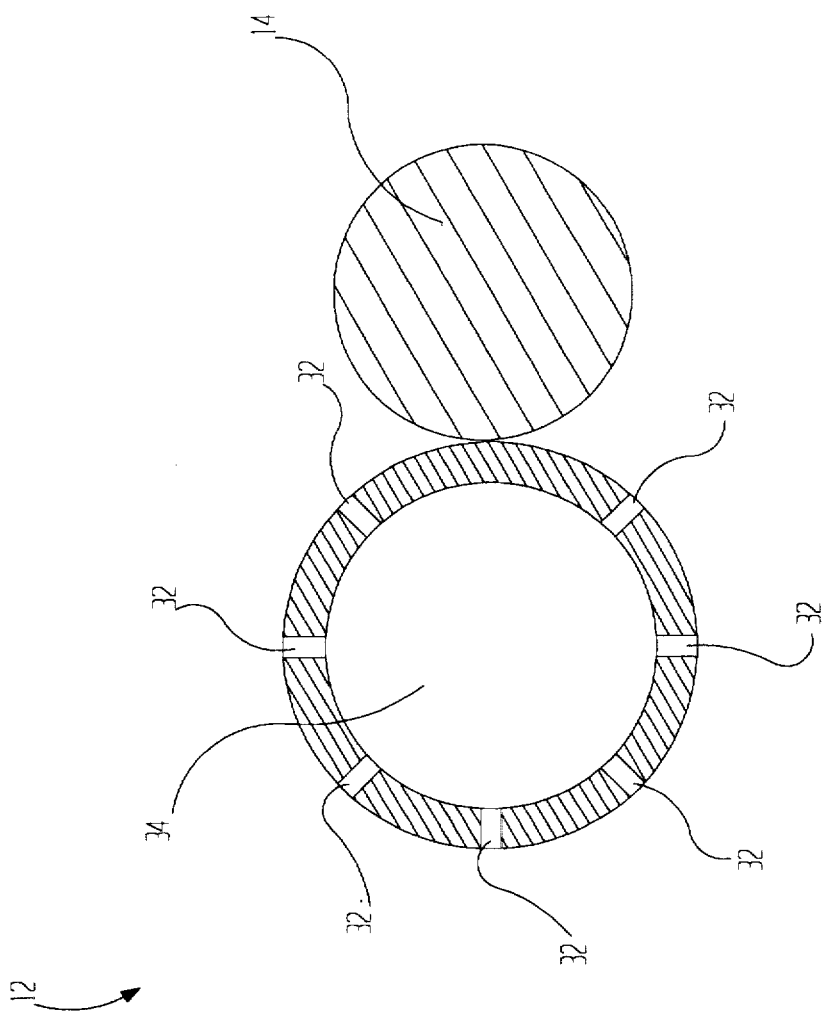
FIG. 4e is a cross sectional view of a fifth embodiment of a port tube of the present invention taken at 4—4 in FIG. 2a and at 4—4 in FIG. 2b.

Referring now to FIG. 4e, a fifth embodiment of the port tube 12 is shown. In this embodiment, the guide wire 14 coextends with the exterior of port tube 12. This embodiment reduces the overall outer diameter of port tube 12 while maintaining similar flow characteristics in the fluid input lumen 34 as compared to the embodiments discussed above. The port tube 12 may include guide loops (not shown) along its length to facilitate advancement along the guide wire 14.

With reference to FIG. 4f, a sixth embodiment of the port tube 12 is shown. The port tube embodiment as shown in FIG. 4f includes a guide wire tube 53 defining a guide wire lumen 35 which is shorter than the overall length of the port tube 12, preferably 3.5 to 10 cm in length. The guide wire tube 53 is preferably an extruded flexible polymer such as polyethylene and is bonded to the port tube 12 but a suitable adhesive or other bonding process. The port tube 12 in this embodiment is preferably made of a stainless steel braid embedded in a thermoset polyimide. A dual lumen extrusion is also feasible for this construction. This feature allows the treating physician to retain a grip of the proximal portion of the guide wire 14 while the port tube 12 is longitudinally manipulated. In addition, since the guide wire tube 53 is less than full length, the extraction lumen 29 is proportionally larger. Alternatively, the extraction tube 13 may be reduced in size without reducing the size of the extraction lumen 29.

Figure 5:
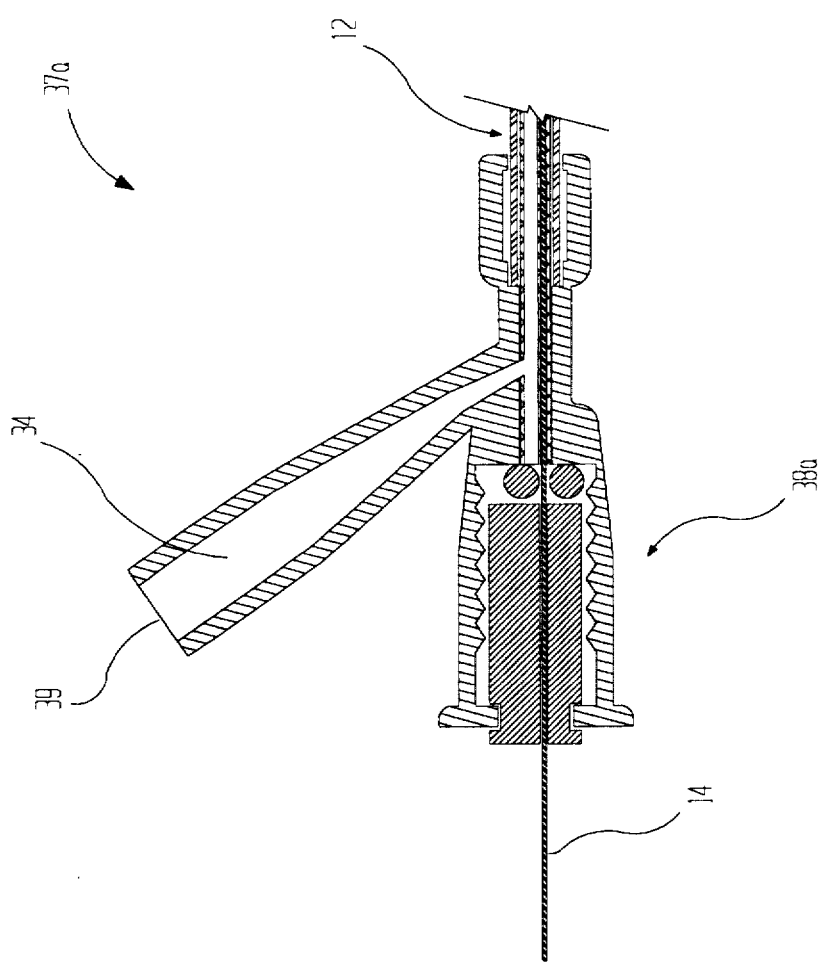
FIG. 5 is a longitudinally sectioned view of a port tube manifold of the present invention.

FIG. 5 shows a port tube manifold 37a connected to the proximal end of port tube 12. The port tube manifold 37a includes a compression seal assembly 38a which releasably and sealably secures to the guide wire 14 which extends therethrough. Port tube manifold 37a further includes a fluid input port 39, preferably a female luer fitting, which facilitates easy connection to the pressurized fluid source 15.

Figure 6:
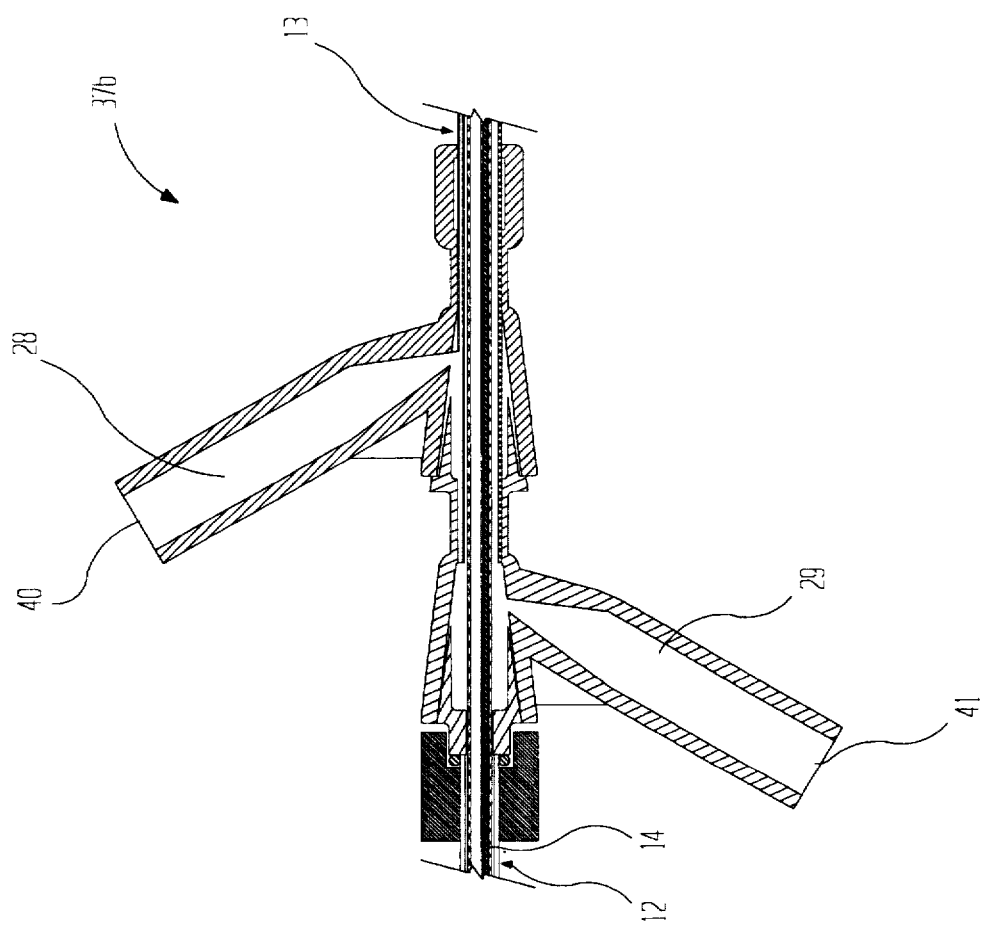
FIG. 6 is a longitudinally sectioned view of an extraction tube manifold of the present invention.

Referring to FIG. 6, extraction tube manifold 37b is connected to the proximal end of extraction tube 13. Port tube 12 extends through the extraction tube manifold 37b and can be releasably and sealably secured by compression seal assembly 38b. Extraction tube manifold 37b includes extraction port 41, preferably a female luer fitting, which facilitates easy connection to the pressurized fluid collector 17. Balloon inflation port 40 is also provided and facilitates easy connection to an inflation device (not shown) in order to selectively inflate and deflate the occluding balloon 27.

Given the preceding detailed description of catheter system 11, a mathematical model of the interaction of fluid system 10 with the vasculature will facilitate a description of control system 16. Assume that the distal end of the catheter system 11 is positioned within a vascular lumen. The occluding balloon 27 is inflated proximal to the occlusive material to be removed. The port tube 12 is positioned such that the port holes 32 are adjacent the occlusive material. The pressurized fluid source 15 and the pressurized fluid collector 17 are activated to establish flow through the port tube 12 and the extraction tube 13. With this arrangement, the operating variables may be defined as follows:

$Q_i$=Volumetric fluid input rate at the distal end of fluid input lumen 34.

$Q_o$=Volumetric fluid (including removed debris) output rate at the distal end of fluid extraction lumen 29.

$Q_i'$=Volumetric fluid input rate at the proximal end of fluid input lumen 34.

$Q_o'$=Volumetric fluid output rate at the proximal end of fluid extraction lumen 29.

$P_1$ is the pressure proximal to the occlusive material.

$P_2$ is the pressure adjacent the occlusive material.

$P_3$ is the intravascular pressure distal of the occlusive material.

$P_o$ is the pressure at the proximal end of the fluid extraction lumen 29.

$P_i$ is the pressure at the proximal end of the fluid input lumen 34.

To maintain a balanced system, $Q_i$ must equal $Q_o$. This flow balance is most critical with total occlusions. To maintain a flow pattern directed from the port holes 32 to the extraction lumen 29, $P_3$ must be greater than $P_2$ and $P_2$ must be greater than $P_1$. Preferably, $P_2$ is only slightly less than $P_3$, on the order of 0.67 psi.

If $P_2$ is less than or equal to $P_1$, the pressurized fluid exiting port holes 32 will either remain stagnant or move in a distal direction, thus increasing the possibility of distal embolization. If $P_3$ is less than or equal to $P_2$, the same result may occur.

If $Q_i$ is greater than $Q_o$, the potential for distal embolization and/or vessel rupture increases. Potential causes for the situation in which $Q_i$ is greater than $Q_o$ include a leak or failure in the pressurized fluid collector system 17 and/or a clogged extraction lumen 29. If $Q_i$ is less than $Q_o$, the potential for vessel collapse increases. The potential causes for $Q_i$ less than $Q_o$ include a leak or failure in the pressurized fluid source 15 and/or a clogged fluid input lumen 34.

Tests have demonstrated that the control system 16 may operate solely as a function of the pressure adjacent the occlusive material ($P_2$). The control system 16 would maintain $P_1$ less than $P_2$ less than $P_3$ by adjusting the appropriate valves to control pressurized fluid source 15 and pressurized fluid collector 17 and thus maintaining fluid flow out the port holes 32 and into the extraction lumen 29. Pressure $P_2$ may be measured by a small pressure transducer mounted on the distal end of the port tube 12. Examples of suitable pressure transducers can be found on catheters available from Millar Instruments, Inc., located in Texas.

Although it would be preferable to monitor fluid dynamic parameters at the distal end of catheter system 11, practical size and cost limitations may be accommodated by locating pressure sensors and volumetric flow sensors at the proximal end of catheter system 11. As such, the possible fluid dynamic parameters to be monitored include $Q_i'$, $Q_o'$, $P_i$ and $P_o$. $Q_i'$ equals $Q_i$ assuming that the pressurized fluid is relatively incompressible at the operating pressures. However, one cannot assume that $Q_o'$ is equal to $Q_o$ because of the possibility of cavitation in the extraction lumen 29. When cavitation occurs, $Q_o'$ is greater than $Q_o$. Potential causes for cavitation include a clogged extraction lumen 29. Because cavitation occurs before a significant difference in $Q_i'$, and $Q_o'$ is detectable, it is necessary to monitor pressures at the proximal end of catheter system 11. During operation, $P_o$ will oscillate in an acceptable pressure window. If $P_o$ decreases outside the acceptable pressure window, cavitation is occurring. As stated before, $Q_i'$ remains substantially equivalent to $Q_o'$ for a period of time despite the occurrence of cavitation in the extraction lumen 29. As such, the immediate detection of cavitation in extraction lumen 29 is only possible by monitoring pressure $P_o$.

With reference now to FIG. 1b, the fluid system 10 includes a control system 16 which is operatively connected to the pressurized fluid source 15 and the pressurized fluid collector 17. Pressurized fluid source 15 is preferably a constant volume pump such as a peristaltic pump, a piston pump, or a diaphragm pump. Pressurized fluid collector 17 includes an aspiration pump 18 which is preferably a constant volume pump such as a peristaltic pump, and a fluid collector 19 which is preferably transparent to allow visualization of the extracted fluid and dislodged occlusive debris. In addition, the entire effluent line defining the extraction lumen 29 (or only the portion proximal of the extraction tube manifold 37b) may be transparent to allow the treating physician to view the removed debris. Control system 16 receives input from pressure sensor 20 which monitors the pressure at the proximal end of extraction lumen 29 ($P_o$ in above model). A diverter valve 21 is also operatively connected to control system 16 and functions to divert pressurized fluid from pressurized fluid source 15 in order to control the volumetric flow rate into fluid input lumen 34.

In this embodiment, the control system 16 maintains balanced volumetric flow (i.e., $Q_i'=Q_o'$ and $Q_i=Q_o$). In the event that a failure or leak in the pressurized fluid collector 17 occurs or in the event that extraction lumen 29 becomes clogged (i.e. $Q_i'>Q_o'$), control system 16 actuates diverter valve 21 so as to reduce $Q_i$ to come into equilibrium with Qo. A means to immediately detect a clogged extraction lumen 29 causing cavitation is provided by pressure sensor 20 which detects an decrease in the pressure ($P_o$) at the proximal end of extraction lumen 29 which is an indicator of cavitation. Control system 16 responds to an increase in pressure as detected by pressure sensor 20 in the same way it responds to $Q_i'>Q_o'$ as discussed above. In the event that a failure or leak in the pressurized fluid source 15 occurs, or in the event that fluid input lumen 34 becomes clogged (i.e., $Q_i<Q_o$), control system 16 shuts down pressurized fluid source 15 and pressurized fluid collector 17.

With reference now to FIG. 1c, the fluid system 10 is substantially the same as that which is shown in FIG. 1b with the following exceptions. Control system 16 is operatively connected to an input flow sensor 23, a modulator valve 24 and a shut-off valve 25 which are positioned between the pressurized fluid source 15 and the fluid input port 39. An output sensor 22 is also operatively connected to the control system 16 and is positioned between the extraction port 41 and the pressurized fluid collector 17. Flow sensors 22 and 23 are preferably ultrasonic volumetric flow sensors such as Model No. 6X available from Transonic Systems, Inc., located in New York. Flow modulator valve 24 and shut-off valve 25 are preferably of the solenoid type. Thus, the fluid dynamic parameter sensors (22, 23) and the flow control valves (24, 25) are electronically controlled by control system 16. If $Q_o'$ as detected by output flow sensor 22 is less than $Q_i'$ as detected by input flow sensor 23, control system 16 proportionately closes modulator valve 24 so as to bring $Q_i'$ into balance with $Q_o'$. If $Q_o'$ is greater than $Q_i'$, control system 16 proportionately opens modulator valve 24 so as to bring $Q_i'$ into equilibrium with $Q_o'$. In the event that $Q_o'$ is greater than $Q_i'$ and the modulator valve 24 is fully open, control system 16 actuates shut-off valve 25 and stops pressurized fluid source 15 and pressurized fluid collector 17 to prevent vessel collapse. As in the fluid system 10 described with reference to FIG. 1b, a pressure sensor (not shown in FIG. 1c) may be incorporated adjacent output flow sensor 22 to detect cavitation in extraction lumen 29 as discussed above. The control system 16 would be operatively connected to the pressure sensor and respond substantially as described with reference to the pressure sensor as shown in FIG. 1b.

Figure 7:
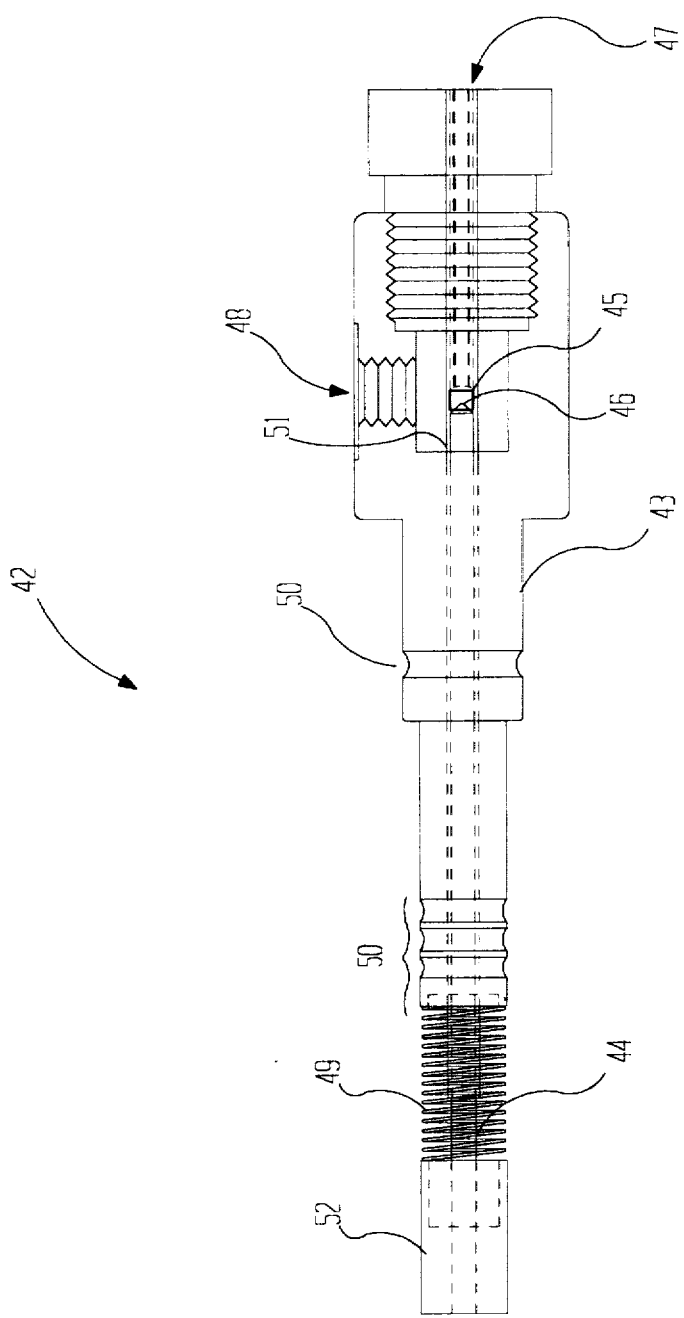
FIG. 7 is a longitudinally partially sectioned view of a modulator valve of the present invention.

Modulator valve 24 is preferably of the solenoid type and is shown in FIG. 7. Referring to FIG. 7, the solenoid modulator valve 42 includes a valve housing 43 and a solenoid shaft 44 slidably disposed in a cylindrical chamber 51. The chamber 51 in valve housing 43 further defines a valve seat 45. The solenoid shaft 44 defines a valve head 46 at the end of the shaft 44 disposed in the chamber 51. The valve housing 43 further includes a fluid input port 48 and a fluid output port 47. The fluid output port 47 is in fluid communication with the valve seat. The fluid input port 48 is in fluid communication with the valve seat (and thus the fluid output port 47) only when the valve head 46 is not positioned in valve seat 45. The valve seat 45 and the valve head 46 are shaped so as to provide a substantially fluid seal when positioned against each other. The solenoid modulator valve 42 further includes a biasing spring 49 disposed between the solenoid head 52 and the valve housing 43. One end of the spring 49 is rigidly connected to the solenoid head 52 and the other end is rigidly connected to the valve housing 43. When the solenoid coil is not activated (i.e. relaxed state), the biasing spring 49 retains the solenoid shaft 44 and valve head 46 in a closed valve position. The valve housing 43 further includes a plurality of recesses 50 for ball detent. The ball detent (not shown) provide a means to releasably secure the solenoid modulator valve 42 in a solenoid coil (not shown). The solenoid coil is actuated by a desired electromotive force, preferably 768 watts, and corresponding driver circuit which in turn longitudinally displaces the low mass solenoid head 52, preferably 2.5 grams in combination with solenoid shaft 44. The high power driver circuit and the low mass solenoid head 52 allow the modulator valve 42 to operate at very high frequencies. The longitudinal actuation of solenoid head 52 causes the solenoid shaft 44 and the valve head 46 to move in and out of valve seat 45. Thus, as the solenoid head 52, solenoid shaft 44, and the valve head 46 longitudinally oscillate, flow is permitted between fluid input port 48 and fluid output port 47 as a function of the period of time that the valve head 46 is not positioned against valve seat 45. The amplitude and frequency of oscillation can be varied by means of an appropriate driver circuit (not shown) operatively connected to the solenoid coil. The solenoid coil is preferably driven by a switching solenoid driver circuit with a frequency between 0.25 cycles per second and 500 cycles per second. Flow is thus modulated by changing the solenoid off-time and on-time. The utilization of biasing spring 49 allows the solenoid coil to be unidirectional and also allows for high operating frequencies.

Figure 8:
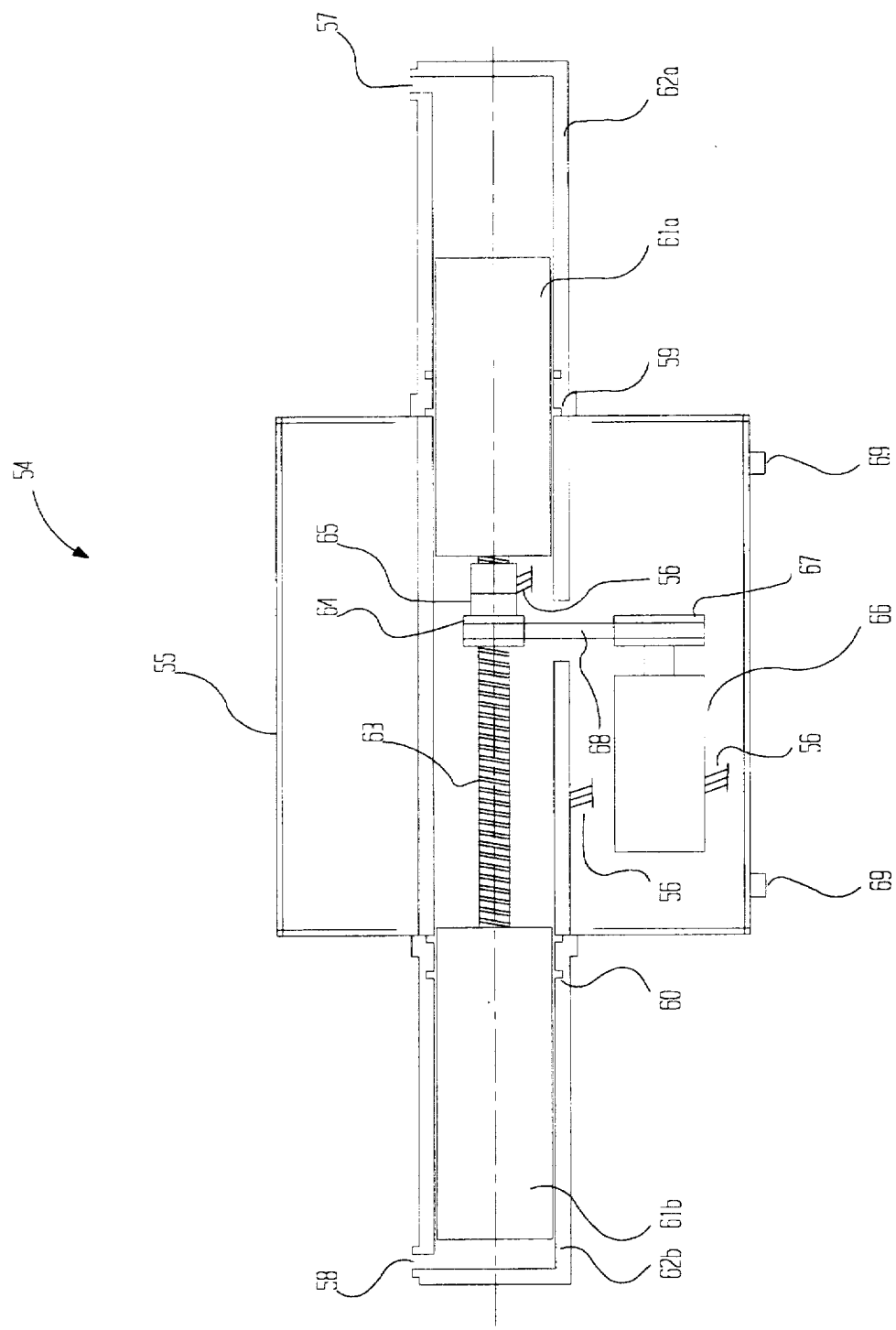

A second preferred fluid system 10 utilizes a double-acting piston pump 54 as seen in FIG. 8. The double-acting piston pump 54 includes a pump housing 55. Pump housing 55 further includes housing feet 69 for securely placing the double-acting piston pump 54 on a level surface. Mechanical grounds 56 shown in FIG. 8 and are intended to schematically reflect a fixed position of components relative to the pump housing 55. Mounted inside pump housing 55 is a stepper motor 66 which rotates pulley 67 which in turn rotates ball screw rotating nut and pulley 64 by way of belt 68. The ball screw rotating nut and pulley 64 axially displaces the threaded shaft 63 relative to the thrust bearing 65 which is mechanically grounded to the housing 65. The threaded shaft 63 in turn is connected to an outlet piston 61a and an inlet piston 61b. A roller pin (not shown) connected to the pistons 61a, 61b and slidably located in a guide slot (not shown) which mechanically grounded to the housing 65 may be used to prevent the pistons 61a, 61b from rotating due to the frictional interface with the threaded shaft 63. The inlet piston 61b is sealably and slidably positioned inside inlet piston chamber 62b, utilizing an O-ring seal 60. Fluid is pulled into the inlet piston chamber 62b by way of inlet port 58. Similarly, outlet piston 61a is slidably positioned inside outlet piston chamber 62a and is sealed by high pressure O-ring or compression seal 59. The pressure seals 59 and 60 may alternatively be disposed on the pistons 61a and 61b. Pressurized fluid exits outlet piston chamber 62a by way of outlet port 57. Outlet port 57 is in turn connected to the fluid input lumen 34 by way of the port tube manifold 37a. Similarly, inlet port 58 is fluidly connected to the extraction lumen 29 by way of the extraction tube manifold 37b.

Inlet piston 61b is preferably made of a polymer and is disposable after a selected number of procedures for sanitary purposes. The inlet chamber 62b is also made of a disposable polymer material and is disposed/replaced along with piston 61b. Outlet piston 61a, outlet piston chamber 62a, the pump housing 55 and associated internal components (56, 63–69) are made of materials conventional in the art (e.g. stainless steel) and are intended to be reusable. The piston chambers 62a and 62b are approximately 1 liter in volume which render them suitable for approximately four procedures before replacement or resetting to starting position becomes necessary. A bio-block filter (not shown), which are known in the art, may be utilized to maintain sterility of the outlet piston 61a and the outlet piston chamber 62a. The bio-block filter would be fluidly connected to the outlet port 57.

The double-acting piston pump 54 offers several advantages over other constant volume pumps. For example, the double-acting piston pump 54 does not require a microprocessor control system. The pressure is controlled by adjusting the torque of the stepper motor 66. When the selected pressure is exceeded and thus the selected torque is exceeded, the stepper motor simply stops rotating and stops movement of outlet piston 61a. Although the outlet piston stops moving a residual pressure will cause a small amount of fluid to egress out of the outlet port 57 for a short period of time after the stepper motor 66 stops rotating. To offset this residual pressure, a suitable electronic or manual on/off valve and vent (not shown) is utilized between the outlet port 57 and the port tube manifold 37a. Thus, when the pressure inside outlet piston chamber 62a exceeds a certain amount as specified by the torque set on the stepper motor 66, the stepper motor shuts down, the valve shuts off and vents excess pressure. A similar valve may be employed in line with the input port 58 to bring residual pressures in the inlet chamber 62b to ambient pressure. As with the other control systems described previously, a pressure transducer located between the inlet port 58 and the extraction manifold 37b may be utilized to detect cavitation. In addition, it is contemplated that the pressure adjacent the distal end of the port tube 12 as measured by a suitable pressure transducer would provide sufficient information to operate the entire system. More specifically, if the measured pressure adjacent the distal end of the port tube 12 falls outside a predetermined acceptable window, the double acting piston pump 54 stops and the valve (preferably a solenoid valve) turns off and vents the system pressure to ambient pressure. The system may then be restarted by actuating the appropriate switches such as a foot pedal switch.

The stepper motor 66 is controlled by a conventional control circuit (not shown) which adjusts torque and speed. The control circuit also includes a switch to allow the treating physician to turn the double-acting piston pump 54 on and off, in addition to forward and reverse. The stepper motor 66 may be reversed to return the pistons 61a, 61b to their initial position. However, because the piston chambers 62a, 62b are relatively large in capacity (preferably 1 liter), the pitons 61a, 61b need not be reset to their starting position until after about four procedures.

Another advantage of the double-acting piston pump 54 over alternative constant volume pumps is that the pump 54 is relatively quiet, which allows the treating physician to focus on the patient and the procedure as a whole. In view of the critical nature of coronary intervention, it is preferable to have as few distractions as possible in the cardiac cath lab.

In practice, the fluid system 10 is used in the following manner. First, a guide wire 14 is inserted into the guide wire lumen 35 such that the guide wire 14 extends out the distal end of the catheter system 11. The catheter system 11 and the guide wire 14 are then inserted into the body either directly into the vasculature or by way of a guide catheter. The distal end of the extraction tube 13 is positioned proximally of the occlusive material to be removed. The occluding balloon 27 is then inflated to isolate a portion of the vasculature distal thereof. The pressurized fluid source 15 and the pressurized fluid collector 17 are then activated in combination with control system 16. As pressurized fluid exits out port holes 32 by way of fluid input lumen 34, the pressurized fluid dislodges and suspends occlusive material. The occlusive material is then removed by way of extraction lumen 29 and is collected in pressurized fluid collector 17. The port tube 12 can be moved independently of aspiration tube 13 in order to remove occlusive material without the need to relocate the aspiration tube 13 and the occluding balloon 27. In the event that the extraction lumen 29 becomes clogged, the port tube 12 can be pulled back such that the port holes 32 are located inside the extraction lumen 29. Thus, the pressurized fluid exiting port holes 32 cause the clogged material to be swept towards the pressurized fluid collector 17. The port tube 12 can then be re-advanced distally of the distal end of extraction tube 13 and occluding balloon 27 to continue the process of removing occlusion material.

Prior to use, the catheter system 11 must be purged in order to remove air from the extraction lumen 29 and the fluid input lumen 34. This may be accomplished by inserting the distal end of the catheter system 11 such that the port holes 32 are located in a reservoir of fluid. The system is then turned on such that pressurized fluid circulates through the fluid input lumen 34 and fluid from the fluid reservoir is pulled into the extraction lumen 29. After running the fluid system 10 for a short period of time, the catheter system 11 is substantially void of gas. After the fluid system 10 is purged, the pressurized fluid source 15, the pressurized fluid collector 17 and the associated control system 16 must be calibrated in order to correctly maintain balanced flow. With the distal end of the catheter system 11 in a small vial with a luer fitting sealably connectable thereto, the pressurized fluid source 16, the pressurized fluid collector 17, and the control system 16 are initiated. The height of the fluid in the vial is monitored and a calibration dial is adjusted on the control system 16 to maintain balanced flow as indicated by a steady height of fluid in the vial. Once the height of the fluid in the vial is constant, the fluid system 10 is calibrated with $Q_i$ equal to $Q_o$.

While the specification describes the preferred designs, materials, methods of manufacture and methods of use, those skilled in the art will appreciate the scope and spirit of the invention with reference to the appended claims.

What is claimed is:

1. A fluid system for the extraction of vascular occluding material, comprising:

a. an elongate catheter shaft having a proximal end and a distal end, the elongate shaft including a fluid input tube and a fluid extraction tube, the fluid input tube being longitudinally movable relative to the fluid extraction tube;

b. the fluid input tube defining a fluid input lumen;

c. the fluid extraction tube defining a fluid extraction lumen;

d. a pressurized fluid source connected to the proximal end of the shaft and in fluid communication with the fluid input lumen;

e. a pressurized fluid collector connected to the proximal end of the shaft and in fluid communication with the extraction lumen;

f. a nozzle attached to the distal end of the fluid input tube and in fluid communication with the fluid input lumen;

g. a control system operatively connected to the pressurized fluid source and the pressurized fluid collector; and h. a fluid dynamic sensor positioned in either the fluid input lumen or the fluid extraction lumen, the fluid dynamic sensor operatively connected to the control system.

2. A fluid system as in claim 1, wherein the fluid dynamic sensor is h. positioned between the fluid extraction lumen and the pressurized fluid collector.

3. A fluid system as in claim 1, wherein the fluid dynamic sensor is i. positioned between the fluid input lumen and the pressurized fluid source.

4. A fluid system as in claim 2, further comprising:

i. a valve positioned between the fluid input lumen and the pressurized fluid source, the valve being controlled by the control system as a function of the fluid dynamic sensor.

5. A fluid system as in claim 1, wherein the fluid input tube is coaxially disposed within the fluid extraction tube.

6. A fluid system as in claim 5, wherein the fluid extraction tube includes an occluding balloon located adjacent the distal end of the fluid extraction tube.

7. A fluid system as in claim 6, wherein the fluid extraction tube includes a laterally facing window located distally of the occluding balloon.

8. A fluid system as in claim 1, wherein the fluid input lumen further defines a guide wire lumen and includes a guide wire extending therethrough.

9. A fluid system as in claim 8, wherein the fluid input tube includes a longitudinal slit which the guide wire may pass through.

10. A fluid system as in claim 8, wherein the fluid input tube includes an exit port which the guide wire may pass through, the exit port located distal of the proximal end of the fluid input tube.

11. A fluid system as in claim 1, wherein the nozzle includes at least one port hole which is directed outwardly.

12. A fluid system as in claim 11, wherein the port hole is directed at least partially proximally.

13. A fluid system as in claim 11, wherein the port hole is directed at an angle to a lateral tangent line on an outer surface of the fluid input tube.

14. A fluid system as in claim 12, wherein the port hole is directed at an angle to a lateral tangent line on an outer surface of the fluid input tube.

15. A fluid system as in claim 11, wherein the nozzle includes a plurality of port holes arranged in a plurality of circumferential rows.

16. A fluid system for the extraction of vascular occluding material, comprising:
   a. an elongate extraction tube having a proximal end, a distal end, and an extraction lumen extending therethrough;
   b. a fluid input tube coextending with the extraction tube and longitudinally movable relative thereto, the fluid input tube having a proximal end, a distal end, and a fluid input lumen extending therethrough;
   c. a pressurized fluid source connected to the proximal end of the fluid input tube and in fluid communication with the fluid input lumen;
   d. a pressurized fluid collector connected to the proximal end of the extraction tube and in fluid communication with the extraction lumen;
   e. a guide wire coextending with the fluid input tube and longitudinally movable relative thereto, and;
   f. a nozzle connected to the distal end of the fluid input tube and in fluid communication with the fluid input lumen.

17. A fluid system as in claim 16, wherein the nozzle includes at least one port hole which is directed outwardly.

18. A fluid system as in claim 17, wherein the port hole is directed at least partially proximally.

19. A fluid system as in claim 17, wherein the port hole is directed at an angle to a lateral tangent line on an outer surface of the fluid input tube.

20. A fluid system as in claim 18, wherein the port hole is directed at an angle to a lateral tangent line on an outer surface of the fluid input tube.

21. A fluid system for the extraction of vascular occluding material, comprising:
   a. an elongate catheter shaft having a proximal end, a distal end, a longitudinal axis, and an outside diameter;
   b. a fluid input lumen extending through the shaft;
   c. an extraction lumen extending through the shaft;
   d. a pressurized fluid source connected to the proximal end of the shaft and in fluid communication with the fluid input lumen;
   e. a pressurized fluid collector connected to the proximal end of the shaft and in fluid communication with the extraction lumen;
   f. a nozzle attached to the distal end of the shaft and in fluid communication with the fluid input lumen, and;
   g. at least one port hole located about the circumference of the nozzle, the port hole having an axis, the port hole directed laterally such that the axis of the hole is at an acute proximally facing angle relative to the longitudinal axis of the shaft and defines a spray diameter which is greater than the outside diameter of the catheter shaft adjacent to the nozzle, the nozzle and port hole being located distally on the shaft such that the spray diameter engages the occluding material before the distal end of the shaft substantially traverses the occluding material.

22. A fluid device as in claim 21, wherein the pressurized fluid source is a constant volume pump.

23. A fluid device as in claim 21, wherein the pressurized fluid collector is a constant volume pump.

24. A fluid device as in claim 21, wherein the pressurized fluid source operates at a pressure substantially within the range of 1 to 2500 psi.

25. A fluid device as in claim 21, wherein the pressurized fluid source operates at a pressure substantially within the range of 500 to 1500 psi.

26. A method of extracting vascular occluding material wherein the vasculature has a first pressure zone with a first pressure proximal to the occluding material, and a second pressure zone with a second pressure adjacent the occluding material, the method comprising the steps of:
   i. providing a fluid extraction system, comprising:
      a. an elongate catheter shaft having a proximal end, a distal end, a fluid input lumen extending therethrough, and an extraction lumen extending therethrough;
      b. a pressurized fluid source connected to the proximal end of the shaft and in fluid communication with the fluid input lumen;
      c. a pressurized fluid collector connected to the proximal end of the shaft and in fluid communication with the extraction lumen;
      d. a nozzle attached to the distal end of the shaft and in fluid communication with the fluid input lumen;
      e. a control system which controls the pressurized fluid source and the pressurized fluid collector as a function of at least one of the first or second pressures; and
      f. at least one port hole located about the circumference of the nozzle, the port hole having an axis, the port hole directed laterally such that the axis of the hole is at an acute proximally facing angle relative to the longitudinal axis of the shaft and defines a spray diameter which is greater than the outside diameter of the catheter shaft adjacent to the nozzle, the nozzle and port hole being located distally on the shaft such that the spray diameter engages the occluding material before the distal end of the shaft substantially traverses the occluding material,
   ii. inserting the catheter into the vasculature; and
   iii. extracting vascular occluding material from the vasculature.

27. A method of extracting vascular occluding material as in claim 26, wherein the control system correlates the first pressure to a first measured fluid dynamic parameter in the extraction lumen.

28. A method of extracting vascular occluding material as in claim 27, wherein the control system correlates the second pressure to a second measured fluid dynamic parameter in the fluid input lumen.

29. A method of extracting vascular occluding material as in claim 26, wherein the control system maintains the first pressure less than the second pressure.

30. A method of extracting vascular occluding material as in claim 26, wherein the control system maintains the second pressure greater than the first pressure.

31. A method of extracting vascular occluding material as in claim 27, wherein the control system maintains equal volumetric flow between the fluid input lumen and the extraction lumen.

32. A method of using a fluid system for the extraction of vascular occluding material wherein the device comprises an elongate catheter shaft having a proximal end and a distal end, a fluid input lumen extending through the shaft, an extraction lumen extending through the shaft, a pressurized fluid source connected to the proximal end of the shaft and in fluid communication with the fluid input lumen, a pressurized fluid collector connected to the proximal end of the shaft and in fluid communication with the extraction lumen, a nozzle attached to the distal end of the shaft and in fluid communication with the fluid input lumen, and a control system operatively connected to the pressurized fluid source and the pressurized fluid collector, the control system controlling the pressurized fluid source and the pressurized fluid collector as a function of fluid dynamic parameters in the fluid input lumen and the fluid extraction lumen, the method of use comprising the steps of:

i. inserting the guide wire into the fluid input tube;

ii. advancing the guide wire, the fluid input tube and the extraction tube into a vascular lumen;

iii. positioning the distal end of the extraction tube proximal to an occlusion to be removed;

iv. positioning the distal end of the fluid input tube adjacent the occlusion to be removed;

v. activating the pressurized fluid source and the pressurized fluid collector; and vi. longitudinally sliding the fluid input tube relative to the extraction tube.

33. A method of using a fluid system as in claim 32, comprising the additional step of:

vii. deactivating the pressurized fluid source and the pressurized fluid collector if the volumetric flow in the extraction lumen is not substantially equal to the volumetric flow in the fluid input lumen.

34. A method of using a fluid system as in claim 32, comprising the additional step of:

vii. longitudinally sliding the fluid input tube in a proximal direction such that the nozzle enters the extraction lumen.

35. A method of using a fluid system for the extraction of vascular occluding material wherein the device comprises an elongate extraction tube having a proximal end, a distal end, and an extraction lumen extending therethrough; a fluid input tube coextending with the extraction tube and longitudinally movable relative thereto, the fluid input tube having a proximal end, a distal end, and a fluid input lumen extending therethrough; a pressurized fluid source connected to the proximal end of the fluid input tube and in fluid communication with the fluid input lumen; a pressurized fluid collector connected to the proximal end of the extraction tube and in fluid communication with the extraction lumen; a guide wire coextending with the fluid input tube and longitudinally movable relative thereto, and; a nozzle connected to the distal end of the fluid input tube and in fluid communication with the fluid input lumen, the method of use comprising the steps of:

i. inserting the guide wire into the fluid input tube;

ii. advancing the guide wire, the fluid input tube and the extraction tube into a vascular lumen;

iii. positioning the distal end of the extraction tube proximal to an occlusion to be removed;

iv. positioning the distal end of the fluid input tube adjacent the occlusion to be removed, and;

v. activating the pressurized fluid source and the pressurized fluid collector.

36. A method of using a fluid system as in claim 35, comprising the additional step of:

vi. longitudinally sliding the fluid input tube relative to the extraction tube.

37. A method of using a fluid system as in claim 36, comprising the additional step of:

vii. deactivating the pressurized fluid source and the pressurized fluid collector if the volumetric flow in the extraction lumen is not substantially equal to the volumetric flow in the fluid input lumen.

38. A method of using a fluid system as in claim 36, comprising the additional step of:

vii. longitudinally sliding the fluid input tube in a proximal direction such that the nozzle enters the extraction lumen.

39. A method of using a fluid system as in claim 38, comprising the additional step of:

viii. longitudinally sliding the fluid input tube in a distal direction such that the nozzle exits the extraction lumen.

* * * * *

UNITED STATES PATENT AND TRADEMARK OFFICE
CERTIFICATE OF CORRECTION

PATENT NO. : 5,536,242

DATED : July 16, 1996

INVENTOR(S) : WILLARD et al.

It is certified that error appears in the above-identified patent and that said Letters Patent is hereby corrected as shown below:

At column 1, line 24, delete "is"; at line 31, "graff" should be --graft--.

Signed and Sealed this

Sixth Day of April, 1999

Attest:

Attesting Officer

Q. TODD DICKINSON

Acting Commissioner of Patents and Trademarks